United States Patent
Li et al.

(10) Patent No.: US 8,477,902 B2
(45) Date of Patent: Jul. 2, 2013

(54) RADIATION INSPECTION APPARATUS AND INSPECTION METHOD FOR OBJECT SECURITY INSPECTION

(75) Inventors: Jianmin Li, Beijing (CN); Yinong Liu, Beijing (CN); Xuewu Wang, Beijing (CN); Ziran Zhao, Beijing (CN); Lan Zhang, Beijing (CN); Yumin Yi, Beijing (CN); Ming Chen, Beijing (CN); Jinyu Zhang, Beijing (CN); Yongming Wang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 13/497,830

(22) PCT Filed: Jun. 25, 2010

(86) PCT No.: PCT/CN2010/074527
§ 371 (c)(1),
(2), (4) Date: May 22, 2012

(87) PCT Pub. No.: WO2011/035624
PCT Pub. Date: Mar. 31, 2011

(65) Prior Publication Data
US 2012/0224671 A1 Sep. 6, 2012

(30) Foreign Application Priority Data

Sep. 25, 2009 (CN) .......................... 2009 1 0093180

(51) Int. Cl.
*H05G 1/02* (2006.01)
(52) U.S. Cl.
USPC .......................................... 378/57; 378/197

(58) Field of Classification Search
USPC .................................................... 378/57, 197
See application file for complete search history.

(56) References Cited

U.S. PATENT DOCUMENTS

| 5,805,662 A | 9/1998 | Kurbatov et al. ............... 378/87 |
| 7,016,473 B1* | 3/2006 | Linev et al. ................... 378/146 |
| 2001/0024484 A1* | 9/2001 | Francke .......................... 378/62 |
| 2007/0086566 A1* | 4/2007 | Gregerson et al. ............. 378/19 |
| 2009/0180593 A1* | 7/2009 | Chen et al. .................... 378/194 |

FOREIGN PATENT DOCUMENTS

| CN | 1739455 | 3/2006 |
| CN | 1829476 A | 9/2006 |
| CN | 101442831 A | 5/2009 |
| CN | 101482523 | 7/2009 |

OTHER PUBLICATIONS

Search Report and Written Opinion from PCT/CN2010/074527, dated Oct. 21, 2010 and Sep. 25, 2012, respectively.

* cited by examiner

*Primary Examiner* — Glen Kao
(74) *Attorney, Agent, or Firm* — Westman, Champlin & Kelly, P.A.

(57) ABSTRACT

The present invention relates to a radiation inspection apparatus for object security inspection, comprising: a ray generator configured to emit a ray, a collimator configured to collimate the ray emitted from the ray generator, and a detector configured to receive the collimated ray collimated by the collimator, wherein the collimated ray forms an irradiated area on the detector included by an effective detect area of the detector. The present invention also relates to a method of performing a security inspection to a body using a radiation inspection apparatus. With the above technical solutions, the present invention can achieve a low single inspection absorptive dose and a micro dose inspection while meeting inspection requirements to improve public radiation security.

14 Claims, 1 Drawing Sheet

RADIATION INSPECTION APPARATUS AND INSPECTION METHOD FOR OBJECT SECURITY INSPECTION

CROSS-REFERENCE TO RELATED APPLICATION

This application is a Section 371 National Stage Application of International Application No. PCT/CN2010/074527, filed Jun. 25, 2010 and published as 2011/035624 on Mar. 31, 2011, in Chinese, the contents of which are hereby incorporated by reference in their entirety.

BACKGROUND OF THE INVENTION

1. Field of the invention

The present invention relates to a radiation imaging detection technology, in particular to a micro dose radiation inspection apparatus for object security inspection, which allows all of rays transmitting through an inspected human body to be collected effectively and be used for imaging.

2. Description of the Related Art

In recent years, as criminal activities, such as by the international terrorist organization, are increasingly rampant, requirements to modern security guaranteeing apparatuses are enhanced. They are required to inspect areas on skins of persons and within bodies of persons. Furthermore, the security guaranteeing apparatuses may be classed into metal and non-metal security inspection apparatuses according to inspection type.

Current metal detectors used widely for inspecting bodies of persons can only find the presence of metals, but they fail to determine the positions and shapes of the metal objects on the bodies. For some dangerous goods, such as plastic explosives and weapons, although they may be inspected and detected, to some extent, by various electronic noses, the electronic noses cannot do anything to plastic weapons and tightly packed bombs. Thus, such dangerous goods typically will be inspected and recognized only by contacting them by inspectors. However, this approach has a low efficiency and causes a significant inconvenience and slight irreverence to all of participants.

In recent years, with development of ion migration spectra (IMS) technology, it becomes possible to detect suspicious particles, such as drugs and explosives, carried by human bodies. For example, an IMS gate type inspection technology may be used, to some extent, to inspect and detect dangerous goods and drugs carried around bodies of persons, but it still fails to inspect dangerous goods and drugs carried within bodies of persons.

At present, only radiation imaging technology, for example, X-ray radiation imaging technology, may meet all of the above requirements for inspection. The basic principle of X-ray radiation imaging technology is that different substances have different absorptive ratios to X-ray emitted from an X-ray source when the X-ray transmits through the bodies of persons to be inspected; and the X-rays which are not absorbed can be converted into electrical signals with various intensities after being collected by detectors, and the electrical signals can be converted into digital signals for display of images by being sampled and processed.

In some of the conventional X-ray radiation imaging body security inspection systems, after transmitting through bodies of persons, the X-rays emitted from the ray source, such as X-ray machine, are collimated and then form a radiation area on a detector, the radiation area including an effective detection area of the detector. Thereby, the part of the X-rays emitted from the ray source and irradiated on the effective detection area of the detector may be sampled and processed, while the part of X-rays which are not irradiated on the detector will not be detected effectively.

Since a considerable part of the X-rays cannot be detected effectively, an absorptive dose for a single inspection has to be enhanced in order to obtain imaging results with same accuracy or sharpness when the bodies are detected in practice. Obviously, it may damage public radiation security. However, if an absorptive dose for a single inspection is reduced, the resulting accuracy or sharpness of the radiation imaging will be reduced inevitably.

Furthermore, in the existing X-ray radiation imaging body security detection processing, the persons to be inspected have to move, while the radiation generator and the detector are kept stationary. In this case, movement of the persons to be inspected may cause a pseudo-image in the collected images, which will seriously degrade qualities of images, including sharpness.

SUMMARY OF THE INVENTION

In view of the above, the present invention is directed to address at least one aspect of the above problems and defects in the prior art.

An object of the present invention is to provide a micro dose radiation inspection apparatus for object security inspection, which can achieve a low single inspection absorptive dose and a micro dose inspection while meeting inspection requirements to improve public radiation security.

Another object of the present invention is to provide a micro dose radiation inspection apparatus for object security inspection, in which a ray source and a detector are operated synchronously, thereby improving quality of radiation imaging.

A further object of the present invention is to provide a micro dose radiation inspection apparatus for object security inspection, in which an electrical synchronization is used while the ray generator and the detector are provided in the form of multibank structure at both ends thereof, in order to rapidly realize field recovery mounting and to increase convenience and range of application of the apparatus.

In accordance with an aspect of the present invention, it provides a radiation inspection apparatus for object security inspection, comprising: a ray generator configured to emit a ray; a collimator configured to collimate the ray emitted from the ray generator; and a detector configured to receive the collimated ray via the collimator, wherein the collimated ray forms an irradiated area on the detector included by an effective detection area of the detector.

In an embodiment, the ray generator, the collimator and the detector are arranged at predetermined intervals in a horizontal direction, the radiation inspection apparatus further comprises a driver configured to drive the ray generator, the collimator and the detector to rise or fall synchronously and vertically.

In a further embodiment, the driver may comprise: a first driving unit configured to drive the ray generator and the collimator to rise or fall vertically; and a second driving unit configured to drive the detector to rise or fall vertically, wherein the first and second driving units drive the ray generator, the collimator and the detector to rise or fall synchronously and vertically by means of a synchronization mechanism.

In a further embodiment, the first driving unit comprises a first motor and a first transmission mechanism connected to the first motor, the ray generator and the collimator being fixed to the first transmission mechanism, and the second driving unit comprises a second motor and a second transmission mechanism connected to the second motor, the detector being fixed to the second transmission mechanism, the synchronization mechanism further comprising: a phasemeter coupled to one of the first motor and the second motor, and a phase following meter coupled to the other of the first motor and the second motor, wherein synchronous movement of the first and second driving units is achieved by adjusting the phase relationship between the phasemeter and the phase following meter.

In a further embodiment, the first transmission mechanism comprises a first lead screw connected to the first motor, a first nut engaged with the first lead screw and a first guide rail guiding the first nut, and the second transmission mechanism comprises a second lead screw connected to the second motor, a second nut engaged with the second lead screw and a second guide rail guiding the second nut, the first lead screw and the second lead screw having a same lead.

In a preferred embodiment, the detector is triggered to collect the ray to form images each time the ray generator, the collimator and the detector rise or fall synchronously and vertically by a predetermined height.

In a further embodiment, a beam exit of the ray generator, a collimating slit of the collimator and a receiving window of the detector are kept in a same plane all along during rising or falling vertically. In an embodiment, a predetermined tilt angle may be formed between the plane and the horizontal plane.

In a further embodiment, the radiation inspection apparatus further comprises an inspection passage through which a person may enter or exit the radiation inspection apparatus, the inspection passage being arranged among the ray generator, the collimator and the detector along the horizontal direction. Alternatively, the inspection passage is provided with a sloped table, on which the person to be inspected stands, at the bottom thereof.

In a preferred embodiment, the detector is a gas detector in which a receiving and detecting area has a thickness of 3 mm in the vertical direction.

In accordance with another aspect of the present invention, it provides a method of performing a security inspection to a body using a radiation inspection apparatus, the radiation inspection apparatus comprising a ray generator configured to emit a ray, a collimator configured to collimate the ray and a detector configured to receive the ray, the method comprising the following steps of (a) driving the ray generator to generate a radiation ray, (b) driving the detector to detect the ray which has been collimated by the collimator and has transmitted through a person to be inspected and (c) processing signals detected by the detector to obtain a radiation imaging unit for inspection, wherein the transmitting ray forms an irradiated area on the detector included by an effective detection area of the detector.

In a further embodiment, the method further comprises the following steps of (d) driving the ray generator, the collimator and the detector to rise or fall synchronously and vertically using a driver and (e) repeating the steps (a)-(c) to obtain a plurality of successive radiation imaging units during performing the step (d).

In a preferred embodiment, the method further comprises repeating the steps (a)-(c) to obtain a plurality of successive radiation imaging units every time the ray generator, the collimator and the detector rise or fall synchronously and vertically by a same predetermined height.

In a further embodiment, the method further comprises adjusting the radiation inspection apparatus or the person to be inspected to allow the ray to irradiate onto the person to be inspected in a direction not perpendicular to the height direction of the person to be inspected.

In a further embodiment, the irradiating in a direction not perpendicular to the height direction of the person may comprise the following steps of providing a sloped table which has a predetermined angle with respect to the horizontal direction, the person to be inspected standing on the sloped table.

In an alternative embodiment, the irradiating in a direction not perpendicular to the height direction of the person may comprise the following steps of adjusting the radiation inspection apparatus to allow a beam exit of the ray generator, a collimating slit of the collimator and a receiving window of the detector to be kept in a same plane all along, wherein a predetermined tilt angle being formed between the plane and the horizontal plane.

Any one aspect of the above technical solutions in the present invention at least has the following benefits and advantages:

In the radiation inspection apparatus and inspection method of the present invention, the ray forms an irradiated area on the detector, which is included by an effective detection area of the detector, after transmitting through the body of the person to be inspected, in contrast to those in which X-ray forms an irradiated area on the detector, which includes the effective detection area of the detector. In other words, the rays reaching the skin of the person to be inspected may all be collected effectively for imaging, except being scattered, to achieve micro dose inspection.

In this way, in contrast to the prior art, the present invention can achieve a low single inspection absorptive dose and a micro dose inspection while meeting inspection requirements, so as to improve public radiation security.

In addition, in the embodiments of the present invention, the ray source and the detector ire operated synchronously while the person to be inspected is stationary, thereby eliminating possible pseudo-image in the collected images to improve the quality of radiation imaging.

Furthermore, the ray generator and the detector of the present invention move synchronously in the vertical direction, and equal levels triggering is used across a scanning region so as to eliminate longitudinal distortion of the scanning images caused by acceleration and deceleration of the scanning move mechanism.

Additionally, in the micro dose radiation inspection apparatus for object security inspection of the present invention, an electrical synchronization is used while the ray generator and the detector are arranged in the form of multibank structure at both ends thereof, in order to rapidly perform field recovery mounting and to increase convenience and range of application of the apparatus.

BRIEF DESCRIPTION OF THE DRAWINGS

The micro dose radiation inspection apparatus and the inspection method for body security inspection according to the embodiments of the present invention will described below with reference to accompanying drawings, in which.

REFERENCE NUMERALS

Figure 1:
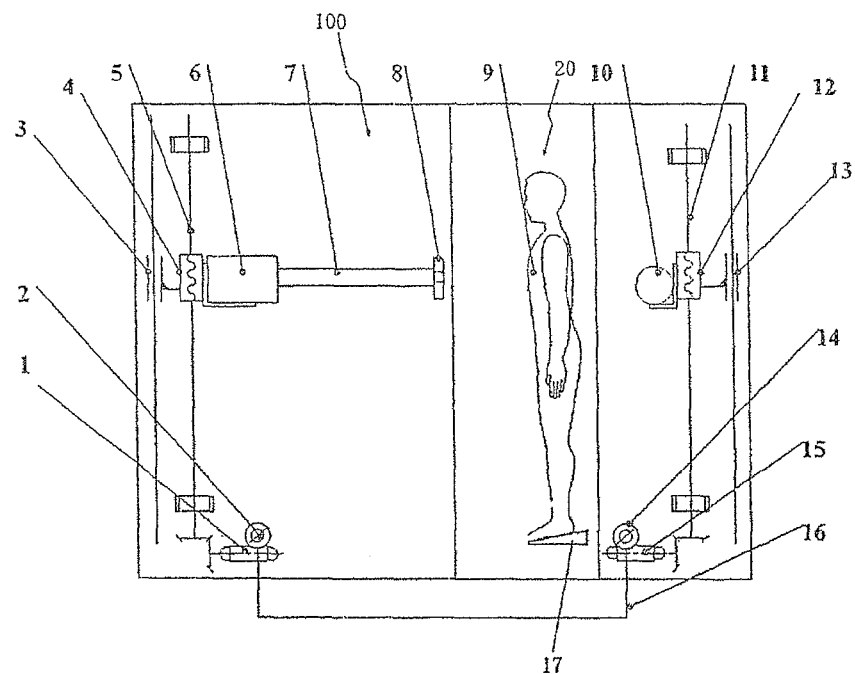
FIG. 1 is a schematic view showing the micro dose radiation inspection apparatus for body security inspection according to an embodiment of the present invention.

1—first motor, 2—phasemeter, 3—first guide rail, 4—first nut, 5—first lead screw, 6—X-ray generator, 7—X-ray shielding box, 8—collimator, 9—person to be inspected, 10—detector, 11—second lead screw, 12—second nut, 13—second guide rail, 14—phase following meter, 15—second motor, 16—phase feedback line.

DETAILED DESCRIPTION OF THE EMBODIMENTS

Specific embodiments of the present invention will be described hereinafter in detail with reference to the accompanying drawings. In the drawings and description, same or similar reference numerals refer to same or similar parts. The embodiments are described below in order to explain the general concept of the present invention without limitations on the scope of the invention.

Figure 2:
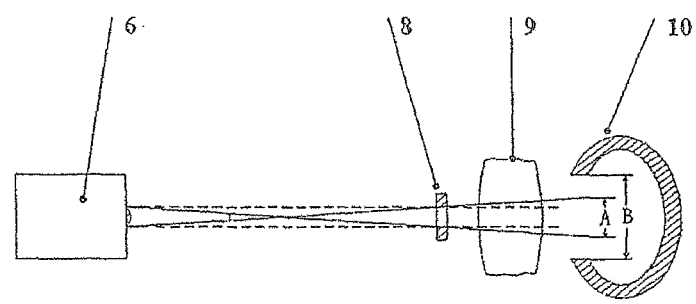
FIG. 2 is a front schematic view showing configuration of the X-ray generator, the collimator and the detector in the micro dose radiation inspection apparatus shown in FIG. 1.

With reference to FIGS. 1-2, a radiation inspection apparatus 100 for body security inspection according to the specific embodiments of the present invention comprises: a ray generator 6 configured to emit a ray, such as X-ray; a collimator 8 configured to collimate the ray emitted from the ray generator, and a detector 10 configured to receive the collimated ray via the collimator. In the radiation inspection apparatus 100, the collimated ray forms an irradiated area A on the detector 10, included by an effective detection area B of the detector 10. In other words, the irradiated area A formed by the collimated ray on the detector 10 has a size less than or equal to that of the effective detect area B of the detector 10.

In the above embodiment, the ray generator 6 is not limited to the X-ray generator. Other ray sources are also applicable, for example, an isotope generator or γ ray generator. The detector 10 may use a solid detector, a liquid detector or a gas detector. For example, the solid detector may comprises a scintillation detector, a semiconductor detector and a thermoluminescent detector. The gas detector may for example be an inert gas ionization chamber.

As illustrated in FIG. 2, in the above embodiment of the present invention, the ray, having transmitted through the body 9 of a person to be inspected, forms the irradiated area A on the detector 10, the irradiated area A being included by the effective detect area B of the detector 10. In other words, the rays reaching the skin of the person to be inspected, except the scattered part, all are collected for imaging to improve the efficiency of rays so as to realize micro dose inspection.

In contrast to the prior art, the effective detect area B of the detector 10 in the present invention has a size equal to or more than that of the irradiated area A formed by the collimated ray on the detector 10. Thus, it is necessary to increase the size of the detector 10. If the same accuracy of the pixel units of the detector is employed, the number of the pixel units of the detector will be increased. Thus, it will significantly increase the cost of the radiation inspection apparatus. If the number of the pixel units of the detector is kept unchanged, the detection accuracy of the pixel units of the detector will be reduced, resulting in reduction of the quality of the images. In view of the above, in a preferred embodiment, a gas detector, for example an inert gas ionization chamber, is used. In particular, as shown in FIG. 2, the detector is a gas detector in which the receiving and detecting area has a thickness of 3 mm in the vertical direction.

In this way, in contrast to the prior art, the present invention can achieve a low single inspection absorptive dose and a micro dose inspection while meeting inspection requirements, so as to improve public radiation security.

As illustrated in FIG. 1, the ray generator 6, the collimator 8 and the detector 10 are arranged at predetermined intervals in a horizontal direction. In an embodiment, the radiation inspection apparatus further comprises an inspection passage 20 through which the person enters and exits the radiation inspection apparatus. The inspection passage 20 is arranged among the ray generator 6, the collimator 8 and the detector 10 in the horizontal direction. In the embodiment shown in FIG. 1, the ray generator 6 and the collimator 8 are fixed to form an integrated configuration by an X-ray shielding box 7. However, the present invention is not limited to this. The ray generator 6 and the collimator 8 may also be combined directly to an integrated configuration, i.e., the X-ray shielding box 7 may be omitted.

Referring to FIG. 1, the radiation inspection apparatus 100 further comprises a driver configured to drive the ray generator 6, the collimator 8 and the detector 10 to rise or fall synchronously and vertically. As an example, the driver may comprise a first driving unit configured to drive the ray generator 6 and the collimator 8 to rise or fall vertically, and a second driving unit configured to drive the detector 10 to rise or fall vertically. The first and second driving units drive the ray generator 6, the collimator 8 and the detector 10 to rise or fall synchronously and vertically by means of a synchronization mechanism. During scanning, the ray generator 6 and detector 10 of the radiation inspection apparatus 100 are kept in synchronization all along. Such synchronization may be achieved by mechanical rigid connection or by electrical synchronization. For example, the mechanical synchronization may be carried out by two groups of lead screws and nuts driven by a same motor.

In an embodiment of the present invention, with reference to FIG. 1, the first driving unit comprises a first motor 1 and a first transmission mechanism connected to the first motor 1. The ray generator 6 and the collimator 8 are fixed to the first transmission mechanism. The second driving unit comprises a second motor 15 and a second transmission mechanism connected to the second motor 15. The detector 10 is fixed to the second transmission mechanism. The synchronization mechanism comprises a phasemeter 2 coupled to the first motor 1 and a phase following meter 14 coupled to the second motor 15. The phase relationship between the phasemeter 2 and the phase following meter 14 is adjusted to achieve a synchronous movement of the first and second driving units. The phasemeter 2 and the phase following meter 14 are not limited to the above configuration. For example, the phasemeter 2 may be coupled to the second motor 15, while the phase following meter 14 may be coupled to the first motor 1.

In the above technical solutions of the present invention, the ray generator 6 and the detector 10 are synchronously operated while the person to be inspected is kept stationary. In this way, possible pseudo-images in the collected images can be eliminated to improve the quality of radiation imaging, compared with the prior art in which the person to be inspected moves while the ray generator and the detector are kept stationary.

As shown in FIG. 1, in a specific embodiment, the first transmission mechanism comprises a first lead screw 5 connected to the first motor 1, a first nut 4 engaged with the first lead screw 5 and a first guide rail 3 guiding the first nut 4. The second transmission mechanism comprises a second lead screw 11, a second nut 12 engaged with the second lead screw 11 and a second guide rail 13 guiding the second nut 12. The first lead screw 5 and the second lead screw 11 have a same lead. In order to ensure synchronization of operations, it is required for the ray generator 6 and the detector 10 to run along a guiding device. In the above embodiments, the guiding device is embodied as guide rails 3 and 13. However, the present invention is not limited to this. For example, a smooth axle passing through the nut 4 or 12 or other devices are also applicable.

In the above embodiment, there is a transmission mechanism for driving, composed of a motor 1, 15, a lead screw 5, 11 and a nut 4, 12, on each of the ray generator 6 side and the detector 10 side. The first motor 1 and the second motor 15 are configured to rotate synchronously by using phase feedback. Preferably, the first motor 1 and the second motor 15 may drive the first lead screw 5 and the second lead screw 11 to rotate, respectively, after being decelerated. As the ray generator 6 side and the detector 10 side have a same reduction ratio, and the lead screws have a same lead, the ray generator 6 side and the detector 10 are operated synchronously, in other words, the embodiment belongs to electrical synchronization.

In a preferred embodiment, the detector 10 is triggered to sample signals to form images every time the ray generator 6, the collimator 8 and the detector 10 rise or fall synchronously and vertically by a predetermined height. In particular, a controlling method can be employed, in which detector collecting signals are triggered by controlling equal movement distances or equal rotating angles of the motors 15 using signals fed back from the phase meter 2 and/or the phase following meter 14. In this way, the image distortion caused by variation of movement speeds or angular speeds may be eliminated. In this embodiment, as a scanning manner of vertically rising and falling is used, the control of triggering the detector collecting signals at equal levels may be used.

Furthermore, the ray generator 6 and the detector 10 of the present invention move synchronously in the vertical direction and use equal levels triggering throughout the scanning region to remove the longitudinal distortions of scanning images caused by acceleration or deceleration of a scanning movement mechanism.

In a further embodiment, with reference to FIGS. 1-2, a beam exit of the ray generator 6, a collimating slit of the collimator 8 and a receiving window of the detector 10 are kept in a same plane all along during rising or falling vertically. With the above solutions, the X-ray emitted from the ray generator 6 is illuminated on the body of the person in the direction perpendicular to the standing direction of the person to be inspected. However, the present invention is not limited to this. The X-ray may be illuminated on the body of the person in the direction not perpendicular to the standing direction of the person to meet the scanning requirements for different parts of the body, such as feet, legs. Correspondingly, in an embodiment, a predetermined tilt angle may be formed between the plane in which the beam exit of the ray generator 6, the collimating slit of the collimator 8 and the receiving window of the detector 10 are located and the horizontal plane.

As an alternative embodiment, the non-normal illumination of the ray may be achieved by the following approach. With reference to FIG. 1, a sloped table 17 on which the person to be inspected stands is provided at the bottom of the inspection passage 20. In this way, the X-ray emitted from the ray generator 6 may is illuminated on all of the body or parts of the body in the direction not perpendicular to the standing direction of the person to be inspected.

A method of performing a security inspection to a body using a radiation inspection apparatus will be explained below in combination with FIGS. 1-2.

As illustrated in FIGS. 1-2, in the method of performing the security inspection to the body using the radiation inspection apparatus 100 of the present invention, the radiation inspection apparatus 100 comprises a ray generator 6 configured to emit a ray, a collimator 8 configured to collimate the ray and a detector 10 configured to receive the ray. The method comprises the following steps of (a) driving the ray generator 6 to generate a radiation ray, (b) driving the detector 10 to detect the ray which has been collimated by the collimator 8 and has transmitted through the person 9 and (c) collecting and processing the detected signal by the detector 10 to achieve radiation imaging unit for inspection, wherein the transmitted ray forms an irradiated area A on the detector 10, and the irradiated area A is included by an effective detection area B of the detector.

In a further embodiment, the method further comprises the steps of driving the ray generator, the collimator and the detector to rise or fall synchronously and vertically using a driver and repeating the steps (a)-(c) to obtain a plurality of successive radiation imaging units while performing the step of driving the ray generator, the collimator and the detector to rise or fall synchronously and vertically.

The above specific operational procedures are provided as follows: the X-ray emitted from the X-ray generator 6 is converted into a sector plane beam via the collimator 8 and transmits through the person 9 and then travels into the receiving window of the detector 10. For example, the detector may be a gas detector in which an insert gas is filled between a high voltage electrode and a collective electrode. After the X-ray enters the receiving window, the insert gas can be ionized. After the high voltage electrode in the detector collects the ionized charges, the electrical signals corresponding to the intensity of the X-ray are generated and these electrical signals are sampled periodically or at equal levels and further converted into digital signals to produce a row of scanning lines for display, i.e., a radiation imaging unit, to perform inspection. The above procedures are repeated during rising or falling vertically and synchronously, and thus several rows of scanning lines may be obtained so as to produce a scanning image, i.e., a plurality of successive radiation imaging units.

As shown in FIG. 1, the driver for driving the ray generator 6, the collimator 8 and the detector 10 to rise or fall vertically and synchronously has the following configurations and is operated as follows.

The first lead screw 5 is rotated by the first motor 1, and the first nut 4 rises or falls along the first guide rail 3 to drive the X-ray generator 6, the X-ray shielding box 7 and the collimator 8 to rise or fall. Similarly, the second lead screw 11 is rotated by the second motor 15, and the second nut 12 rises or falls along the second guide rail 13 to drive the detector 10 to rise or fall. The rotating angle signal of the second motor 15 is fed back in real time to the phasemeter 2 of the first motor 1 via the phase following meter 14 so as to achieve the synchronization rotation of the first motor and the second motor. Thus, the synchronously rising or falling of the X-ray generator 6, the X-ray shielding box 7, the collimator 8 and the detector 10 are achieved.

In a preferred embodiment, the steps (a)-(c) may be repeated to obtain a plurality of successive radiation imaging units every time the ray generator 6, the collimator 8 and the detector 10 are driven to rise or fall synchronously and vertically by a same predetermined height, and thus obtaining a scanning image of the object to be inspected.

As described above, the radiation inspection apparatus or the person to be inspected may be adjusted to allow the ray to be irradiated on the person 9 to be inspected in a direction not perpendicular to the lengthwise direction of the person 9. In a further embodiment, as shown in FIG. 1, the irradiating on the person in a direction not perpendicular to the lengthwise direction of the person may comprise the step of providing a sloped table 17 which has a predetermined angle with respect to the horizontal direction, the person 9 standing on the sloped table. Alternatively, the irradiating on the person in a direction not perpendicular to the lengthwise direction of the person may comprise the step of adjusting the radiation inspection apparatus 100 to allow the beam exit of the ray generator 6, the collimating slit of the collimator 8 and the receiving window of the detector 10 to be kept in a same plane all along, a predetermined tilt angle being formed between the plane and the horizontal plane.

Although in the above embodiments of the present invention, the principles of the present invention have been explained with reference to the vertical direction and the horizontal direction shown in FIGS. 1 and 2, the vertical direction and the horizontal direction herein is only illusive instead of limiting. The synchronous movement of the ray generator and the detector in the radiation inspection apparatus 100 may be vertical movement, or may be other forms of movements, for example, horizontal movement or swing.

Although the above embodiments are explained with reference to the body of person, it is apparent that the present invention is not limited to this, for example, it may be directed to animals or other objects.

Although the general concept and some specific embodiments of the present invention have been described and illustrated, it is appreciated by the skilled person in the art that modifications to the above embodiments can be carried out without departing the spirit and the principle of the present invention. The scope of the present invention is defined by the appended claims and their equivalents.

The invention claimed is:

1. A radiation inspection apparatus for object security inspection, comprising:
   a ray generator configured to emit an x-ray,
   a collimator configured to collimate the x-ray emitted from the x-ray generator,
   a detector configured to receive the collimated x-ray collimated by the collimator wherein the ray generator, the collimator and the detector are arranged at predetermined intervals in a horizontal direction, and,
   wherein the collimated x-ray forms an irradiated area on the detector, the irradiated area being included by an effective detection area of the detector;
   a driver configured to drive the x-ray generator, the collimator and the detector to rise or fall synchronously and vertically, wherein the driver comprises:
      a first driving unit configured to drive the x-ray generator and the collimator to rise or fall vertically, and
      a second driving unit configured to drive the detector to rise or fall vertically,
      wherein the first and second driving units drive the ray x-ray generator, the collimator and the detector to rise or fall synchronously and vertically by a synchronization mechanism, wherein:
         the first driving unit comprises a first motor and a first transmission mechanism connected to the first motor, the x-ray generator and the collimator being fixed to the first transmission mechanism, and
         the second driving unit comprises a second motor and a second transmission mechanism connected to the second motor, the detector being fixed to the second transmission mechanism,
      the synchronization mechanism comprises a phasemeter coupled to one of the first motor and the second motor, and a phase following meter coupled to the other of the first motor and the second motor, wherein the phase relationship between the phasemeter and the phase following meter is adjusted to achieve a synchronous movement of the first and second driving units.

2. The radiation inspection apparatus for object security inspection according to claim 1, characterized in that
   the first transmission mechanism comprises a first lead screw connected to the first motor, a first nut engaged with the first lead screw and a first guide rail guiding the first nut, and
   the second transmission mechanism comprises a second lead screw connected to the second motor, a second nut engaged with the second lead screw and a second guide rail guiding the second nut,
   wherein the first lead screw and the second lead screw have a same lead.

3. The radiation inspection apparatus for object security inspection according to claim 1, characterized in that the detector is triggered to collect the x-ray to form images every time the x-ray generator, the collimator and the detector are driven to rise or fall synchronously and vertically by a predetermined height.

4. The radiation inspection apparatus for object security inspection according to claim 1, characterized in that a beam exit of the x-ray generator, a collimating slit of the collimator and a receiving window of the detector are kept in a same plane all along during rising or falling vertically.

5. The radiation inspection apparatus for object security inspection according to claim 4, characterized in that a predetermined tilt angle is formed between the plane and the horizontal plane.

6. The radiation inspection apparatus for object security inspection according to claim 1, characterized in that the radiation inspection apparatus further comprises an inspection passage through which a person is allowed to enter or exit the radiation inspection apparatus, the inspection passage being arranged among the x-ray generator, the collimator and the detector along the horizontal direction.

7. The radiation inspection apparatus for object security inspection according to claim 6, characterized in that the inspection passage is provided with a sloped table, on which the person to be inspected stands, at the bottom thereof.

8. The radiation inspection apparatus for object security inspection according to claim 1, characterized in that the detector is a gas detector in which a receiving and detecting area has a thickness of 3 mm in the vertical direction.

9. A method of performing a security inspection to a body using a radiation inspection apparatus according to claim 1, the method comprising the following steps of:
   (a) driving the ray generator to generate a radiation x-ray,
   (b) driving the detector to detect the x-ray which has been collimated by the collimator and has transmitted through a person to be inspected, and
   (c) processing the detected signal by the detector to achieve a radiation imaging unit for inspection,
   (d) driving the x-ray generator, the collimator and the detector to rise or fall synchronously and vertically using a driver, and
   (e) repeating the steps (a)-(c) to obtain a plurality of successive radiation imaging units while performing the step (d).

10. The method of performing a security inspection to a body using a radiation inspection apparatus according to claim 9, characterized in that the method further comprises repeating the steps (a)-(c) to obtain a plurality of successive radiation imaging units every time the x-ray generator, the collimator and the detector are driven to rise or fall synchronously and vertically by a same predetermined height.

11. The method of performing a security inspection to a body using a radiation inspection apparatus according to claim 9, characterized in that the method further comprises the step of:
(f) adjusting the radiation inspection apparatus or the person to be inspected to allow the x-ray to irradiate on the person to be inspected in a direction not perpendicular to the lengthwise direction of the person.

12. The method of performing a security inspection to a body using a radiation inspection apparatus according to claim 11, characterized in that the step (f) comprises the steps of
providing a sloped table which has a predetermined angle with respect to the horizontal direction, the person standing on the sloped table.

13. The method of performing a security inspection to a body using a radiation inspection apparatus according to claim 11, characterized in that the step (f) comprises the steps of
adjusting the radiation inspection apparatus to allow a beam exit of the x-ray generator, a collimating slit of the collimator and a receiving window of the detector to be kept in a same plane all along, a predetermined tilt angle being formed between the plane and the horizontal plane.

14. The method of performing a security inspection to a body using a radiation inspection apparatus according to claim 9, characterized in that the detector is a gas detector in which a receiving and detecting area has a thickness of 3 mm in the vertical direction.

* * * * *